US00PP22569P2

(12) United States Plant Patent
Jansen

(10) Patent No.: US PP22,569 P2
(45) Date of Patent: Mar. 6, 2012

(54) ***PENSTEMON* PLANT NAMED 'STRAWBERRY TAFFY'**

(50) Latin Name: ***Penstemon* spp.**
Varietal Denomination: Strawberry Taffy

(75) Inventor: Robert D. Jansen, Beaverton, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/927,594

(22) Filed: Nov. 17, 2010

(51) Int. Cl.
*A01H 5/00* (2006.01)

(52) U.S. Cl. ..... Plt./465

(58) Field of Classification Search ..... Plt./465
See application file for complete search history.

*Primary Examiner* — Annette Para
(74) *Attorney, Agent, or Firm* — Jondle & Associates, P.C.

(57) ABSTRACT

A new and distinct cultivar of *Penstemon* plant characterized by large purple red flowers with white throats with a deep purple red ring at the top of the throat, dense flower clusters, long bloom time, a compact, upright, well branched habit, with multiple crown from the base, clean-looking, deep green, attractive foliage, and excellent vigor.

1 Drawing Sheet

Botanical denomination: *Penstemon* spp.
Variety designation: 'Strawberry Taffy'.

BACKGROUND OF THE INVENTION

The present invention relates to a new and distinct cultivar of *Penstemon*, given the name, 'Strawberry Taffy'. *Penstemon* is in the family Scrophulariaceae. This plant originated from an open pollinated cross using *Penstemon* 'Raspberry Flair', an unpatented plant, as the seed parent. This cultivar was selected for its compact growing habit, large flowers in dense clusters, long flowering time, vigor, and clean attractive look. It is an ideal plant for a sunny border in full sun.

Compared to the seed parent, *Penstemon* 'Raspberry Flair', an unpatented plant, the new cultivar has much longer bloom time, longer inflorescences, more stems from the crown, and a more spreading habit.

Compared to *Penstemon* 'Pheni Magna' (U.S. Plant Pat. No. 17,987), the new cultivar has a more compact habit and flowers that are a darker red tone and have a dark ring at the top of the white eye, rather than no dark ring. The new cultivar does not require pinching to branch.

*Penstemon* 'Strawberry Taffy' is uniquely distinguished by its:

1. large purple red flowers with white throats with a deep purple red ring at the top of the throat;
2. dense flower clusters;
3. long bloom time;
4. compact, upright, well branched habit, with multiple crown from the base;
5. clean-looking, deep green, attractive foliage; and
6. excellent vigor.

The new variety has been reproduced only by asexual propagation (cuttings and micropropagation). Each of the progeny exhibits identical characteristics to the original plant. Asexual propagation by cuttings and micropropagation using terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

FIG. 1 shows a close up of a one year old *Penstemon* 'Strawberry Taffy' in the summer in Canby, Oreg.

FIG. 2, foreground, shows a two year old *Penstemon* 'Strawberry Taffy' in bloom growing in full sun in the trail bed in July in Canby, Oreg.

DETAILED PLANT DESCRIPTION

The following is a detailed description of the new *Penstemon* cultivar based on observations of two-year-old specimens grown outside in the ground in the trial beds in Canby, Oreg. in late June. The color descriptions are all based on The Royal Horticultural Society Colour Chart, 5$^{th}$ edition.

Plant:

*Type*.—Herbaceous perennial.
*Form*.—Upright, branching.
*Cold hardiness*.—USDA Zone 7-10.
*Size*.—Grows to 46 cm wide and 58 cm high.
*Vigor*.—Excellent.
*Stem number*.—20 stems from the crown.
*Stem*.—Upright, grows to 40 cm long and 5 mm wide (at the base), pubescent, internodes grow to 5 cm long, Yellow Green 146C.
*Rooting*.—Plants root easily from stem cuttings.

Leaf:

*Type*.—Simple.
*Arrangement*.—Opposite.
*Shape*.—Lanceolate.
*Venation*.—Pinnate.
*Margins*.—Entire to sparsely denticulate.
*Apex*.—Acuminate.
*Base*.—Sessile.
*Blade size*.—Grows to 12 cm long and 3 cm wide.
*Surface texture*.—Glabrous on both sides.
*Leaf color*.—Topside Green 137A, bottom side Green 137B.

Inflorescence:

*Type*.—Terminal, many flowered, dense thyrse.

*Number of flowers per inflorescence*.—26 on average.

*Size of inflorescence*.—Grows to 18 cm long and 10 cm wide.

*Peduncle*.—Grows to 3 cm long and 4 mm wide, pubescent, Yellow Green N144A tinted Red Purple 59A in sun.

*Pedicel*.—Grows to 17 cm long and 1 mm wide, pubescent, Yellow Green N144A tinted Red Purple 59A in sun.

*Bloom period*.—June through September in Canby, Oreg. if spent blooms are removed.

Flower bud:

*Size*.—3.5 cm long and 15 mm wide.

*Description*.—Closed tubular, bulging, flattened ventrically.

*Color*.—White NN155A except Red Purple 63B on lobes and bottom.

Flower:

*Type*.—Zygomorphic, perfect.

*Shape*.—Tubular, bilabiate.

*Size*.—Grows to 4 cm long and 4.5 cm wide.

*Corolla description*.—Grows to 4 cm long and 4.5 cm wide; tube is funnel-form in the calyx for 6 mm long and 4 mm wide, inflating for 25 mm long to 25 mm wide, flaring into 5 lobes, the two smaller top lobes flare back (17 mm wide and 17 mm deep) and two larger lateral lobes flare out (20 mm wide and 20 mm deep), and the lower lobe flares down (17 mm wide and 17 mm deep), lobe margins entire, tips obtuse; outside pubescent, inside glabrous; outside Red Purple 63A on top of funnel and top 2 lobe backs, Red Purple 63B on bottom 3 lobe backs, White NN155C on funnel bottom; inside color is Red Purple 63A on lobes outer ¾, 3 bottom lobes have a ring of Red Purple 60A which extends down their main vein, tube is White NN155D with bee tracks of Red Purple 61A.

*Calyx description*.—10 mm deep and 7 mm wide, 5 overlapping lobes cut to the base, each lobe broadly ovate in shape, 10 mm deep and 9 mm wide, margins entire, tip acute, base cuneate, Yellow Green 145A and pubescent inside and outside, outside tip and sometimes margins Greyed Purple N186C.

*Pistil description*.—1, 32 mm long, ovary 7 mm long and 3 mm wide, Yellow Green 145A; style 25 mm long and less than 1 mm wide, White NN155C.

*Stamen description*.—5, one sterile without an anther, held within the corolla, filaments 2.5 to 4 cm long and White NN155C, anthers 3 mm wide and 1.5 mm deep, Greyed Purple N186D, pollen White NN155C.

*Fragrance*.—Slight.

*Lastingness*.—A flower lasts 5 to 6 days.

Fruit:

*Type*.—Capsule.

*Fertility*.—Good.

*Size*.—1.2 cm deep and 4 mm wide.

*Color*.—Brown 200A to B.

Seed:

*Shape*.—Irregular.

*Size*.—2 mm long.

*Color*.—Brown 200A.

Pests and diseases:

Excellent disease tolerance to root rot, a common problem for *Penstemon*. Leaf spot, rust, and powdery mildew may be a problem, but have not been observed on the new cultivar. No known disease or pest resistances.

I claim:

1. A new and distinct cultivar of *Penstemon* plant substantially as shown and described.

* * * * *

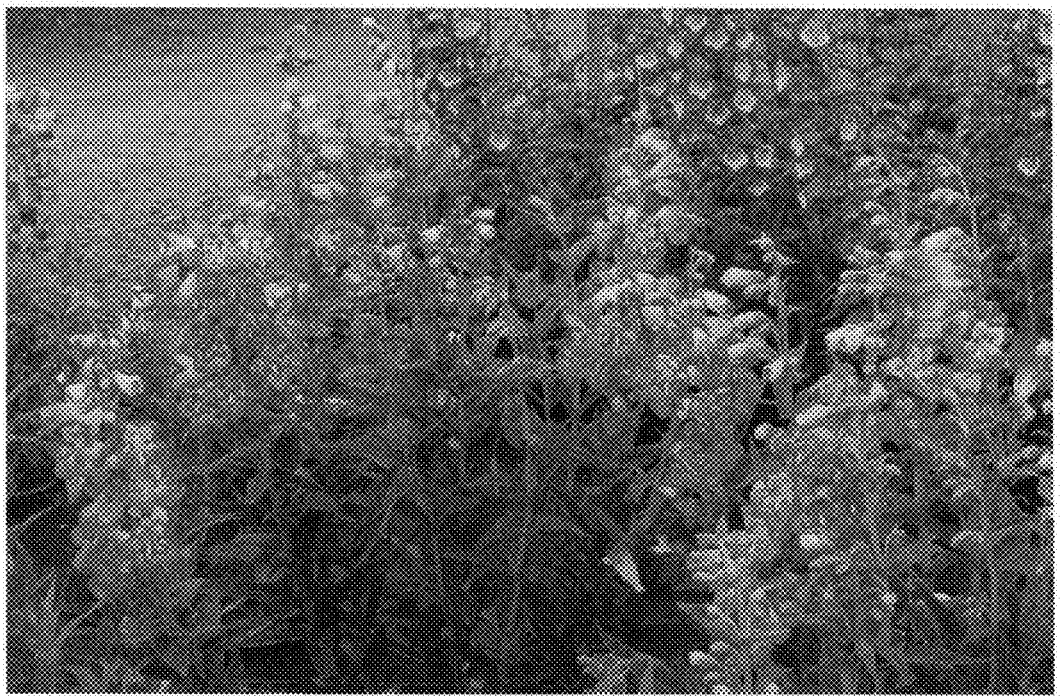

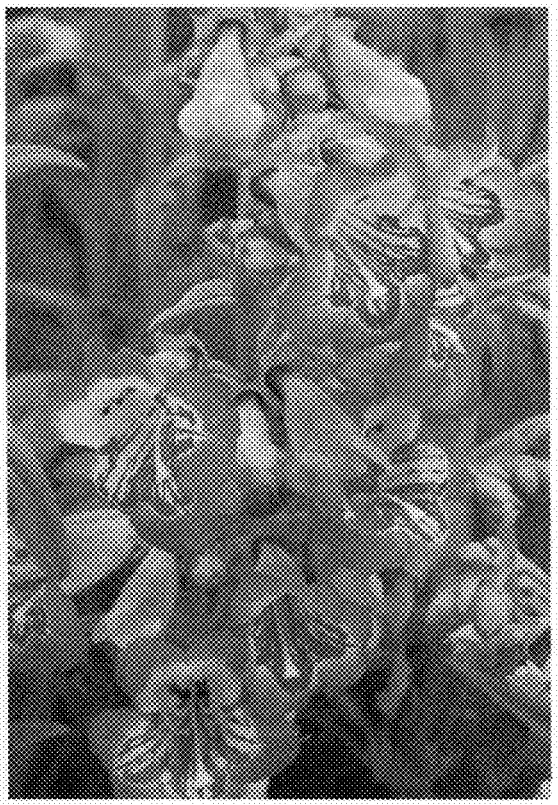
Figure 1 to left
Figure 2 below